(12) United States Patent
Dixon

(10) Patent No.: US 8,522,647 B1
(45) Date of Patent: Sep. 3, 2013

(54) ECCENTRIC GEAR FOR TATTOO MACHINE FOR ADJUSTING THE NEEDLE THROW

(76) Inventor: Alan B. Dixon, Destin, FL (US)

( * ) Notice: Subject to any disclaimer, the term of this patent is extended or adjusted under 35 U.S.C. 154(b) by 202 days.

(21) Appl. No.: 13/136,585

(22) Filed: Aug. 5, 2011

(51) Int. Cl.
*B43K 5/00* (2006.01)

(52) U.S. Cl.
USPC ................................. 81/9.22; 30/362; 606/186

(58) Field of Classification Search
USPC ........... 81/9.22; 606/186; 30/362; 604/289, 604/47, 48
See application file for complete search history.

(56) References Cited

U.S. PATENT DOCUMENTS

| | | | |
|---|---|---|---|
| 464,801 A | 12/1891 | O'Reilly | |
| 498,519 A | 5/1893 | Lewis et al. | |
| 768,413 A | 8/1904 | Wagner | |
| 4,159,659 A | 7/1979 | Nightingale | |
| 4,204,438 A * | 5/1980 | Binaris et al. | 81/9.22 |
| 4,782,725 A * | 11/1988 | Spaulding | 81/9.22 |
| 5,401,242 A | 3/1995 | Yacowitz | |
| 5,551,319 A | 9/1996 | Spaulding | |
| 6,282,987 B1 | 9/2001 | Moniz | |
| 6,392,460 B1 | 5/2002 | Vail | |
| 7,207,242 B1 * | 4/2007 | Daigle | 81/9.22 |
| 7,748,294 B2 | 7/2010 | Jarboe et al. | |
| 7,922,688 B2 | 4/2011 | Bodduluri et al. | |
| 2008/0078271 A1 | 4/2008 | Atkinson | |
| 2010/0192730 A1 | 8/2010 | Dubin | |

* cited by examiner

*Primary Examiner* — David B Thomas
(74) *Attorney, Agent, or Firm* — Peter Loffler

(57) ABSTRACT

An eccentric gear for a tattoo machine allows the throw of the needle of the machine to be quickly and easily changed without the need to adjust the springs of the machine. The eccentric gear, which is rotatably connected to the output shaft of the motor and also to the linkage bar, has a body member that has a channel on its upper surface. A slide plate, to which the linkage bar is rotatably connected, is slidably disposed within the channel so that movement of the linkage bar-slide plate connection point closer to or farther away from the longitudinal axis of the output shaft, decreases or increases the throw of the needle respectively. A set screw frictionally locks the slide plate within the channel.

4 Claims, 5 Drawing Sheets

ECCENTRIC GEAR FOR TATTOO MACHINE FOR ADJUSTING THE NEEDLE THROW

BACKGROUND OF THE INVENTION

1. Field of the Invention

The present invention relates to an eccentric gear for a tattooing machine wherein the depth of throw of the needle is adjustable by the operator via the eccentric gear.

2. Background of the Prior Art

In recent years, tattooing has come into the main stream. No longer relegated to bikers and sailors on leave, tattoos are a popular form of self-expression in middle class America. A tattooed body has gained acceptance among "normal" people.

Essentially human tattooing involves one or more needles that repeatedly penetrate a person's skin, depositing a bit of ink with each penetration. A handle held tattooing machine uses a motor that reciprocates the needle arrangement up and down in order to perform the penetration strokes. The up and down stroke distance of the needle arrangement, the throw, is variable depending on the type of inking stroke being performed. In modern tattooing, there are three main inking strokes, namely outline, shading, and coloring. Each type of stroke requires a different configuration for the tattoo machine. In performing outlining, a single needle is typically used. As only a single needle is being used to penetrate the skin, the throw need not be great in order to achieve proper skin depth penetration of the needle. The next type of stroke is outlining wherein a set of multiple needles are used. As multiple needles are being used to simultaneously penetrate the skin, the throw given by the machine needs to be greater than the throw used for one needle outlining strokes in order to achieve proper skin penetration by the needles. The last type of stroke is the coloring stroke wherein multiple needles in a greater number than the number of needles used for shading, are used. As an even greater number of needles is being used penetrate the skin, the throw needs to be greater than the throw used for shading strokes in order to achieve proper skin penetration by the needles.

In order to change the needle throw for a particular type of stroke, the tattoo machine must be adjusted. This adjustment involves resetting the springs used to hold the armature bar of the machine and the process is extremely time-consuming and frustrating, especially if it must be performed multiple times for a single tattoo job, especially considering the fact that each adjustment must be made with a high degree of precision in order to achieve the proper throw for the stroke to be performed. Having an incorrect throw for a given pass can result in a highly substandard ink application and a highly irate customer. As such, many tattoo artists simply have three tattoo machines at the ready for each job, one adjusted for outlining strokes, one for shading strokes, and one for coloring strokes. Having three separate machines available eliminates the need for on the fly adjustments and speeds up the overall process. However, this arrangement is costly in that three machines need to be purchased and maintained and cleaned after each job.

What is needed is a tattoo machine wherein the needle throw can be adjusted as needed for the particular type of stroke to be performed. Such a device must allow for rapid and easy throw adjustment that allows the throw to be set with a high degree of precision.

SUMMARY OF THE INVENTION

The eccentric gear for a tattoo machine for adjusting the needle throw of the present invention addresses the aforementioned needs in the art by providing a typical tattoo machine with the ability to dynamically adjust the needle throw of the machine quickly and easily and with a high degree of precision. The eccentric gear for a tattoo machine for adjusting the needle throw requires little modification from the standard machine configuration so that the device is not unduly expensive to obtain. Eliminating the need for either time-consuming and frustrating throw adjustments as currently performed, or the use of three machines for a given job, increases the throughput of each job and reduces the overall costs of a given job.

The present invention is comprised of an eccentric gear for a tattoo machine, such that the tattoo machine has a frame that holds motor, the motor turning an output shaft. The eccentric gear is rotatably attached to the output shaft while a linkage bar has a first end rotatably attached to the eccentric gear and also has a second end rotatably attached to an armature bar. The armature bar is connected to the frame via a spring. A needle has a proximal end rotatably connected to the armature bar and also has a pointed distal or working end. The eccentric gear is comprised of a body member that has a lower surface that is rotatably connected to the output shaft and an upper surface such that a channel is disposed within the upper surface and is oriented radially with respect to a longitudinal axis of the output shaft. A slide plate is slidably disposed within the channel such that the linkage bar is connected to the slide plate. A set screw is threadably disposed within the slide plate and capable of frictionally engaging the body member in order to hold the slide plate in a fixed position within the channel.

BRIEF DESCRIPTION OF THE DRAWINGS

Similar reference numerals refer to similar parts throughout the several views of the drawings.

DESCRIPTION OF THE PREFERRED EMBODIMENT

Figure 1:
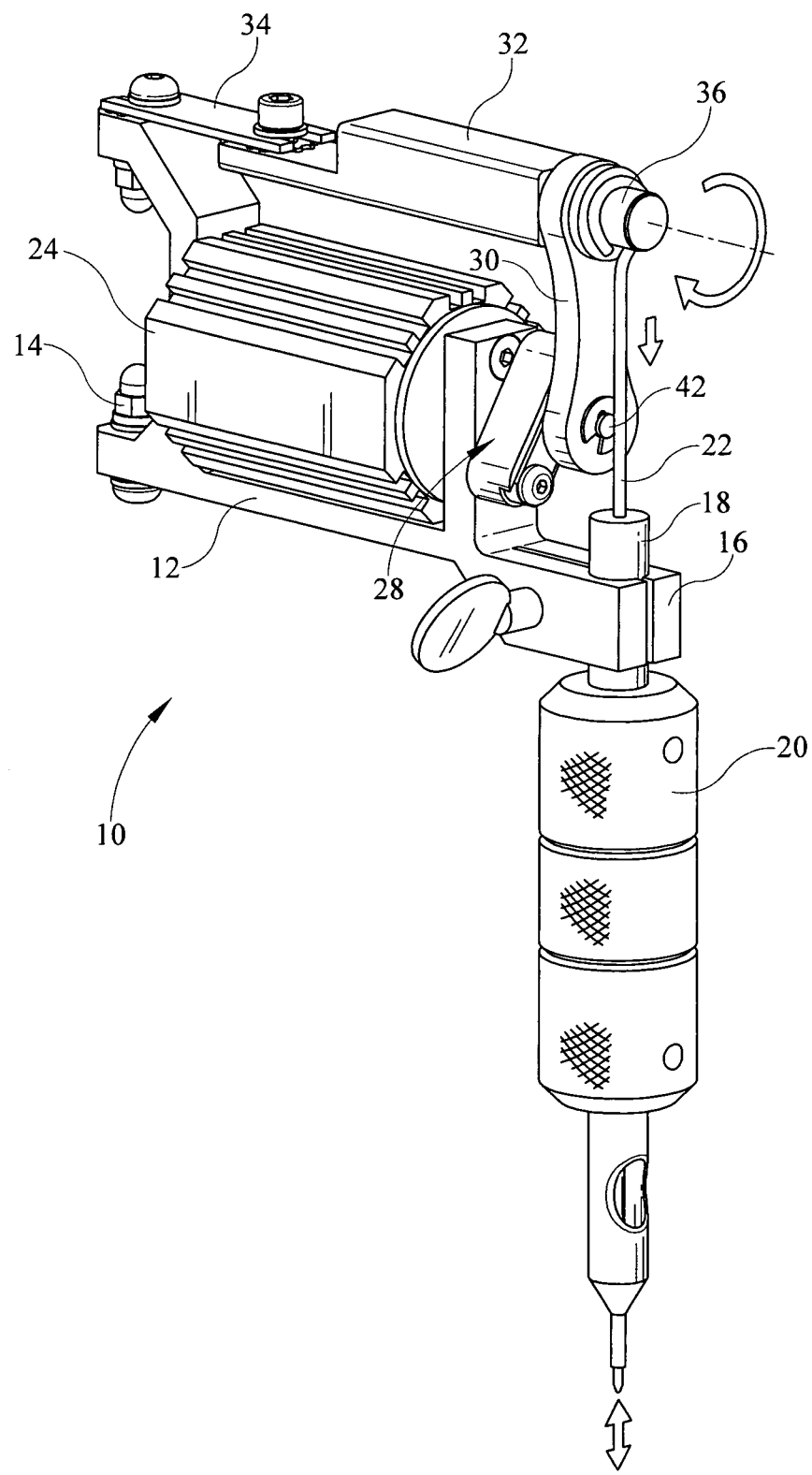
FIG. 1 is a perspective view of the eccentric gear for a tattoo machine for adjusting the needle throw of the present invention during the down portion of a stroke.
Figure 2:
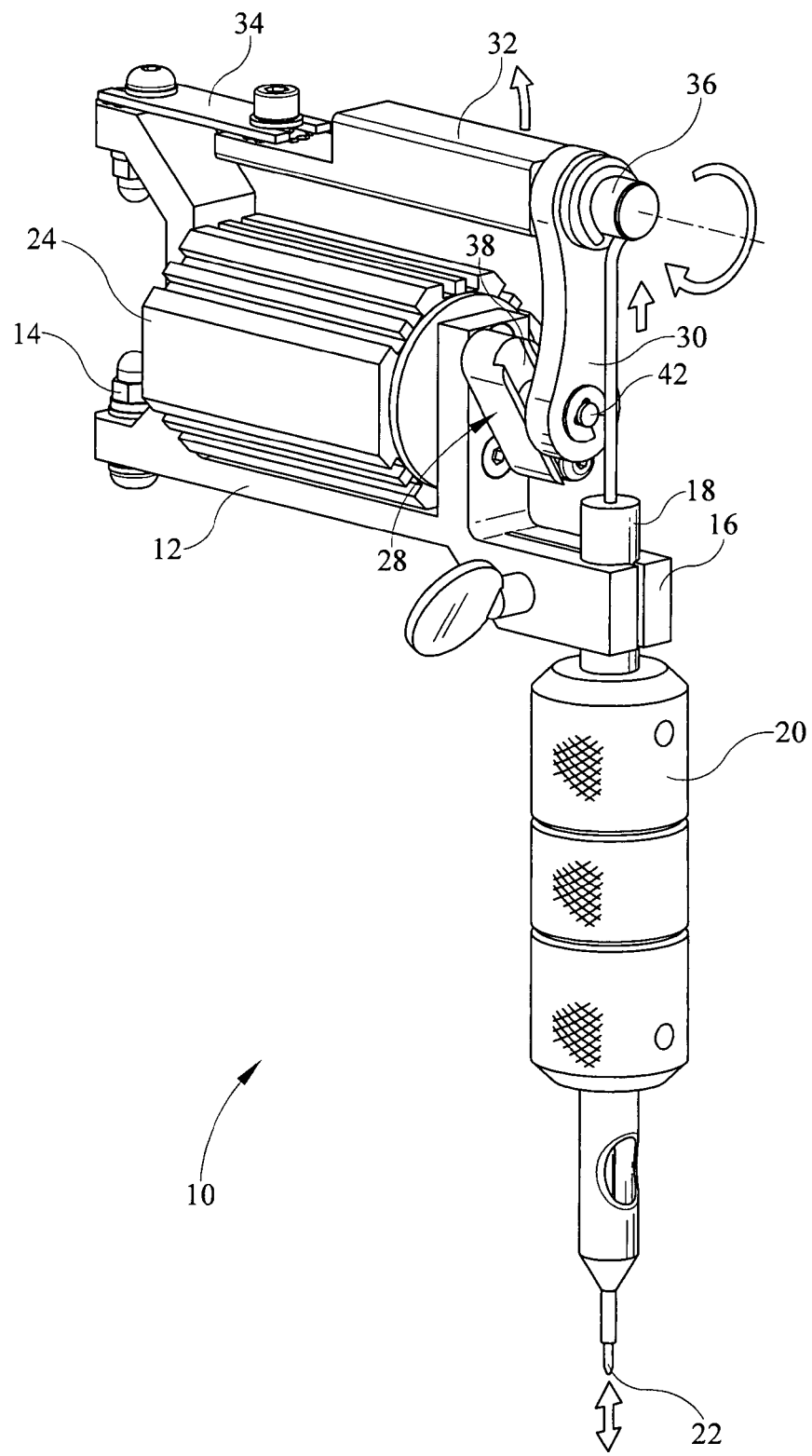
FIG. 2 is a perspective view of the eccentric gear for a tattoo machine for adjusting the needle throw during the up portion of a stroke.
Figure 3:
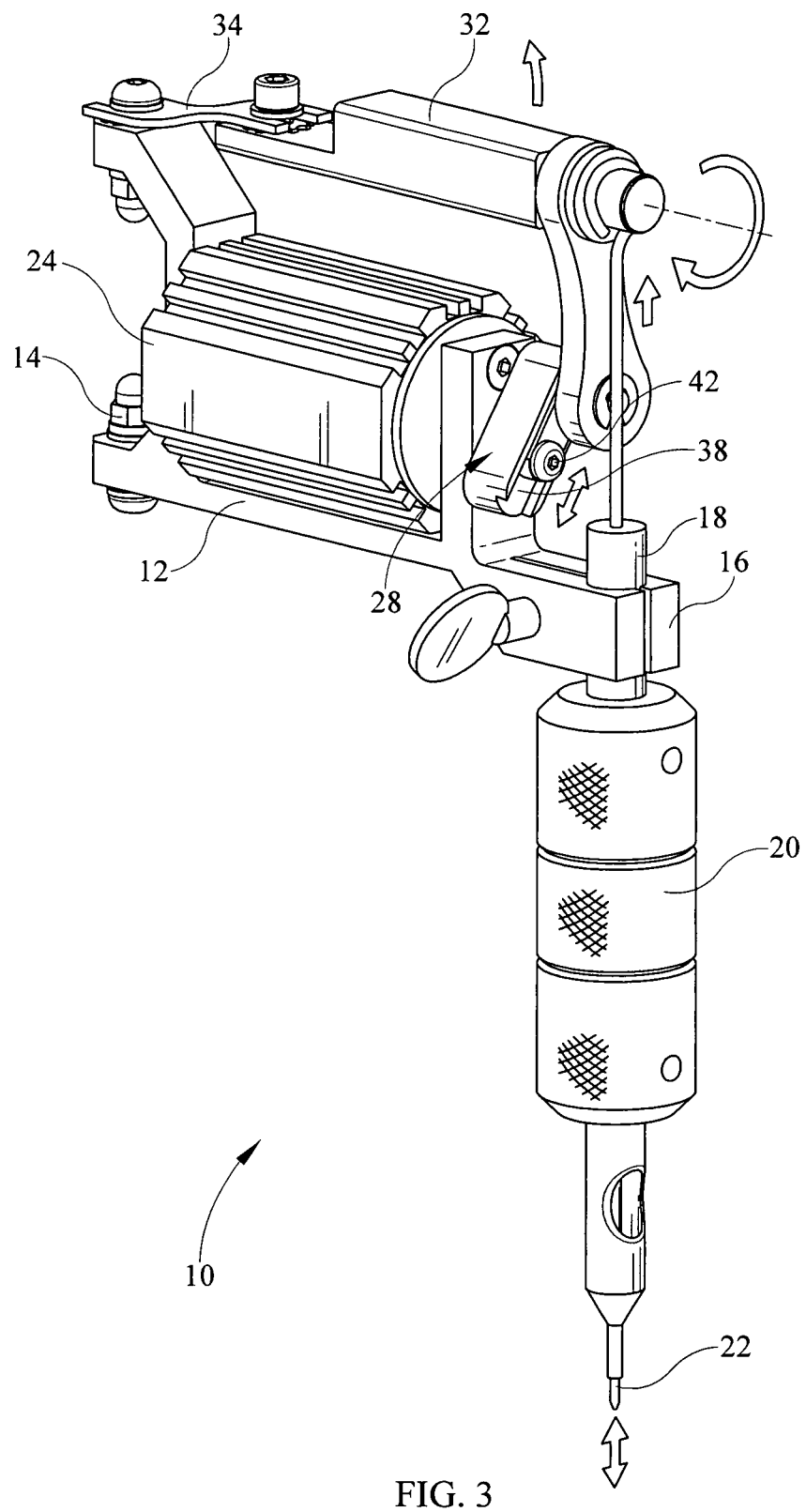
FIG. 3 is a perspective view of the eccentric gear for a tattoo machine for adjusting the needle throw with the throw of the needle increased relative to the throw illustrated in FIGS. 1 and 2.
Figure 4:
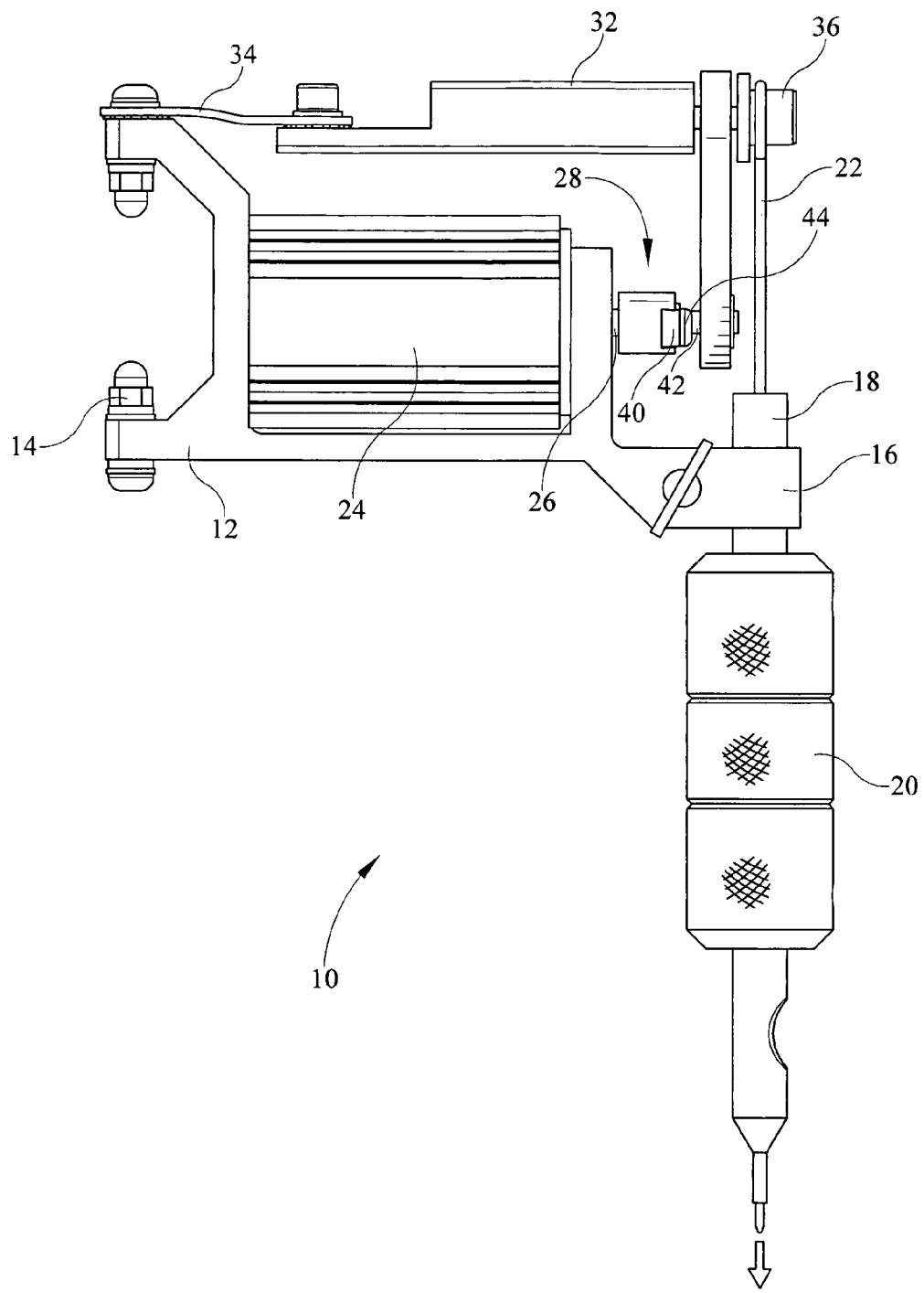
FIG. 4 is a side view of the eccentric gear for a tattoo machine for adjusting the needle throw.
Figure 5:
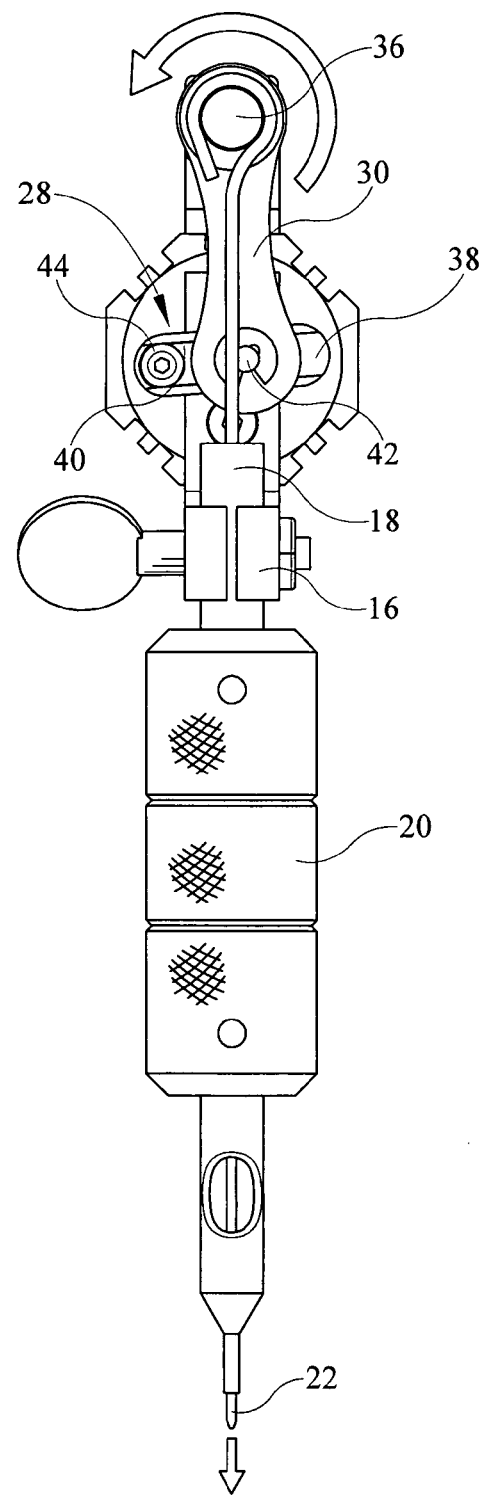
FIG. 5 is a front view of the eccentric gear for a tattoo machine for adjusting the needle throw.

Referring now to the drawings, it is seen that the eccentric gear for a tattoo machine for adjusting the needle throw of the present invention, generally denoted by reference numeral 10, is comprised of a typical tattoo machine arrangement and includes a frame 12, a rear bearing post 14, a tube clamp 16 holding a tube 18, a grip 20 through which one or more needles 22 passes, a motor 24 having an output shaft 26 that is connected to an eccentric gear 28, the eccentric gear 28 pivotally connected to a linkage bar 30, the linkage bar 30 pivotally connected to an armature bar 32, which is connected back to the frame 12 via a spring 34. The various controls and electrical connects, being standard, are not illustrated. The proximal end of the needle 22 is mounted to a top hat grommet 36 on the end of the armature bar 32. As the motor 24 operates, the output shaft 26 rotates, causing eccentric rotation of the eccentric gear 28. Rotation of the eccentric gear 28 causes the linkage bar 30 to stroke up and down, which causes the needle 22 to stroke up and down.

As seen, the eccentric gear 28 has a channel 38 located on its top surface, (the surface opposite the surface to which the output shaft 26 is connected. A slide plate 40 is slidably disposed within the channel 38 with the pivotal connection of the eccentric gear 28 with the linkage bar 30 being made via the slide plate 40 via a shaft 42 that extends upwardly from the slide plate 40 and passes through the linkage bar 30, appropriately secured thereafter. A set screw 44 passes through the slide plate 40 and frictionally engages the eccentric gear.

In use, the slide plate 40 is slid into a desired position within the channel 38 in order to set the throw of the needle 22. By positioning the slide plate 40 to be such that the attachment point of the slide plate 40 and the linkage bar 30 is relatively farther from the longitudinal axis of the output shaft 26, then the linkage bar 30 makes a relatively greater circumference of travel during each rotation of the eccentric gear 28. As such, the linkage bar 30 makes a relatively greater up and down distance of travel during each eccentric gear 28 rotation so that this greater stroke distance travel translates to a greater throw of the needle 22 attached to the top end of the linkage bar 30. By moving the attachment point of the slide plate 40 and the linkage bar 30 to be relatively closer to the longitudinal axis of the output shaft 26, then the linkage bar 30 makes a relatively smaller circumference of travel during each rotation of the eccentric gear 28. As such, the linkage bar 30 makes a relatively lesser up and down distance of travel during each eccentric gear 28 rotation so that this lesser stroke distance travel translates to a lesser throw of the needle 22 attached to the top end of the linkage bar 30. When the position of the slide plate 40 is in the desired position, the set screw 44 is turned so as to frictionally engage the eccentric gear 26 in order to hold the slide plate 40 in position. When the needle 22 throw needs to be changed, the set screw 44 is counter-turned in order to allow the slide plate 40 to slide, the slide plate 40 is slid into its next desired position, and the set screw 44 is once again rotated in order to lock the slide plate 40 into this new position.

While the invention has been particularly shown and described with reference to an embodiment thereof, it will be appreciated by those skilled in the art that various changes in form and detail may be made without departing from the spirit and scope of the invention.

I claim:

1. An eccentric gear for a tattoo machine, the tattoo machine having a frame holding a motor that turns an output shaft, the eccentric gear rotatably attached to the output shaft, a linkage bar having a first end rotatably attached to the eccentric gear, and a second end rotatably attached to an armature bar, the armature bar connected to the frame via a spring, a needle having a proximal end rotatably connected to the armature bar and a pointed distal end, the eccentric gear comprising:

a body member having a lower surface that is connected to the output shaft and an upper surface, such that a channel is disposed within the upper surface and is oriented radially with respect to a longitudinal axis of the output shaft; and a slide plate slidably disposed within the channel such that the linkage bar is connected to the slide plate.

2. The eccentric gear as in claim 1 further comprising a set screw threadably disposed within the slide plate and capable of frictionally engaging the body member in order to hold the slide plate in a fixed position within the channel.

3. The eccentric gear as in claim 1 in combination with the tattoo machine.

4. The eccentric gear as in claim 3 further comprising a set screw threadably disposed within the slide plate and capable of frictionally engaging the body member in order to hold the slide plate in a fixed position within the channel.

* * * * *